United States Patent [19]

Braig et al.

[11] Patent Number: 5,313,941
[45] Date of Patent: May 24, 1994

[54] NONINVASIVE PULSED INFRARED SPECTROPHOTOMETER

[76] Inventors: James R. Braig, 6147 Chelton Dr., Oakland, Calif. 94611; Daniel S. Goldberger, 644 College Ave., Boulder, Colo. 80302

[21] Appl. No.: 10,634

[22] Filed: Jan. 28, 1993

[51] Int. Cl.$^5$ ............................................. A61B 5/00
[52] U.S. Cl. .................................... 128/633; 128/664; 128/666; 128/667; 356/41
[58] Field of Search ............................... 128/633–635, 128/664–667; 356/39–41

[56] References Cited

U.S. PATENT DOCUMENTS

| | | |
|---|---|---|
| 3,958,560 | 5/1976 | March . |
| 4,223,680 | 9/1980 | Jobsis ................................. 128/633 |
| 4,281,645 | 8/1981 | Jobsis ................................. 128/633 |
| 4,407,290 | 10/1983 | Wilber ............................... 128/633 |
| 4,655,225 | 4/1987 | Dahne et al. ...................... 128/633 |
| 4,714,080 | 12/1987 | Edgar, Jr. et al. ................. 128/633 |
| 4,819,752 | 4/1989 | Zelin ................................. 128/633 |
| 4,934,372 | 6/1990 | Corenman et al. ................ 128/633 |
| 4,960,126 | 10/1990 | Conlon et al. .................. 128/666 X |
| 5,009,230 | 4/1991 | Hutchinson ........................ 128/633 |
| 5,028,787 | 7/1991 | Rosenthal et al. ................. 250/341 |
| 5,078,136 | 6/1992 | Stone et al. ..................... 128/666 X |
| 5,081,998 | 1/1992 | Yelderman et al. ............... 128/719 |
| 5,095,913 | 3/1992 | Yelderman et al. ............... 128/719 |
| 5,111,817 | 5/1992 | Clark et al. .................... 128/666 X |
| 5,137,023 | 8/1992 | Mendelson et al. ............... 128/633 |

FOREIGN PATENT DOCUMENTS

WO81/00622  3/1981  Fed. Rep. of Germany .

Primary Examiner—Angela D. Sykes
Attorney, Agent, or Firm—Woodcock, Washburn, Kurtz, Mackiewicz & Norris

[57] ABSTRACT

A method and apparatus for monitoring glucose, ethyl alcohol and other blood constituents in a noninvasive manner. The measurements are made by monitoring infrared absorption of the desired blood constituent in the long infrared wavelength range where the blood constituent has a strong and distinguishable absorption spectrum. The long wavelength infrared energy is passed through a finger or other vascularized appendage and the measurement made. To prevent the high energy source from burning or causing patient discomfort, only short bursts or pulses of energy are sent through the finger with a very low duty cycle and low optical bandwidth. The bursts are further synchronized with systole and diastole of the cardiac cycle so that only two pulses are sent per heart beat, one during diastole and one during systole. The detection signals measured during application of these bursts of energy are then used to calculate the concentration of the blood constituents in accordance with a polynomial equation.

26 Claims, 6 Drawing Sheets

NONINVASIVE PULSED INFRARED SPECTROPHOTOMETER

BACKGROUND OF THE INVENTION

1. Field of the Invention

The present invention relates to an instrument and a method for noninvasively measuring the concentration of glucose, dissolved carbon dioxide, ethyl alcohol or other constituents in a patient's blood. In particular, the present invention relates to an instrument and associated method for monitoring the infrared absorption of such constituents in a patient's blood at long infrared wavelengths where such constituents have strong and distinguishable absorption spectra by passing long wavelength infrared energy through a finger or other vascularized appendage of the patient and measuring the resultant absorption.

2. Brief Description of the Prior Art

Infrared detection techniques have been widely used for the calculation of oxygen saturation and the concentration of other blood constituents. For example, noninvasive pulse oximeters have been used to measure absorption signals at two or more visible and/or near infrared wavelengths and to process the collected data to obtain composite pulsatile flow data of a patient's blood. Sample pulse oximeters of this type are described by Corenman et al. in U.S. Pat. No. 4,934,372; by Edgar, Jr. et al. in U.S. Pat. No. 4,714,080; and by Zelin in U.S. Pat. No. 4,819,752.

Infrared detection techniques have also been used to calculate the concentrations of constituents such as nitrous oxide and carbon dioxide in the expired airstream of a patient. For example, Yelderman et al. describe in U.S. Pat. Nos. 5,081,998 and 5,095,913 techniques for using infrared light to noninvasively measure the absolute concentrations of the constituents of the respiratory airstream of a patient by placing an infrared transmission/detection device on the artificial airway of the patient. These infrared detection techniques and those described above have proven to be quite accurate in the determination of arteriole blood oxygen saturation, the patient's pulse, and the concentrations of carbon dioxide, nitrous oxide and other respiratory constituents.

Spectrophotometric methods have also been used to noninvasively monitor the oxidative metabolism of body organs in vivo using measuring and reference wavelengths in the near infrared region. For example, Jobsis describes in U.S. Pat. Nos. 4,223,680 and 4,281,645 a technique in which infrared wavelengths in the range of 700–1300 nm are used to monitor oxygen sufficiency in an organ such as the brain or heart of a living human or animal. In addition, Wilber describes in U.S. Pat. No. 4,407,290 a technique in which visible and near infrared light emitting diodes and detection circuitry are used to noninvasively measure changes in blood thickness of predetermined blood constituents relative to total change in blood thickness at a test area so as to determine the concentration of such constituents in the blood. Such constituents include hemoglobin and oxyhemoglobin, and the measured concentrations are used to determine the oxygen saturation of the blood. Wilber further suggests at columns 11–12 that such techniques may be extended to the measurement of glucose in the bloodstream; however, Wilber does not tell how to make such measurements, what wavelengths of energy to use, or the form of the mathematics necessary for the calculation of glucose concentration.

Extension of the noninvasive blood constituent measuring techniques described above for use in measuring glucose concentration in the bloodstream is highly desirable. According to the American Diabetes Association, more than 14 million people in the United States have diabetes, though about half of them are not aware of it. Almost 750,000 people per year are diagnosed with diabetes, while approximately 150,000 die from the disease or its complications each year. Since people with diabetes are at risk for blindness, kidney disease, heart disease and stroke, they need to control the disease by closely monitoring their blood glucose levels and carefully controlling the intake of insulin and glucose. Numerous home diagnostic devices have been developed for this purpose.

For example, conventional procedures used to measure glucose levels in the bloodstream include biochemical, electrochemical and spectroscopic techniques. The biochemical techniques measure the glucose oxidase reaction and are widely used in laboratories and in conventional consumer glucose monitoring instruments such as the One Touch ® glucose monitor manufactured by LifeScan, Inc. Although relatively accurate, this technique requires a sample of blood to be withdrawn from the patient and applied to a chemically reactive test strip. The repeated withdrawal of blood samples is less than desirable. The electrochemical techniques, on the other hand, do not require the withdrawal of blood. However, these techniques typically require the surgical implantation of glucose electrodes and cells in the patient for use in providing signals to a regulated insulin reservoir (such as an artificial pancreas). While these techniques show great promise for use in implants and automatic insulin control systems, the associated systems are relatively inaccurate, insensitive and not very selective. Obviously, this technique is quite invasive; nevertheless, it is useful in the case of severe diabetes were the sensor can be implanted together with the electronically regulated insulin reservoir or artificial pancreas to form a complete closed loop system for severely affected diabetics.

Spectroscopic glucose monitoring techniques using infrared light are presently believed to be the most accurate and are the subject of the present application. Unlike the noninvasive oxygen saturation measurement techniques described above, prior art spectroscopic glucose monitoring techniques have typically used extra-corporeal "flow through" cells that allow continuous measurements using infrared light. Indeed, attenuated total internal reflection (ATR) cells have been employed in the long wavelength infrared to measure the glucose content of extracted blood samples. However, such techniques also require samples of blood to be taken from the patient and are thus undesirable for widespread consumer use.

Laser Raman Spectroscopy is another spectroscopic technique which uses a visible spectrum range stimulus and the visible red spectrum for measurement. As with ATR cells, extra-corporeal blood is also used with Raman technology to make the glucose measurements. However, the Raman technique is based upon the principle that over the entire visible spectrum range whole blood has a high absorption due to haemoglobin and other chromophores which produce a high fluorescence background making detection of bands that are not resonance amplified very difficult. Sub-nanosecond laser pulses are used to overcome some of these problems; however, this technology is quite complex and expensive.

Another spectroscopic technique offers a non-invasive solution to the problem of measuring glucose in the bloodstream. According to this technique, near infrared spectroscopy, light is passed through a finger or suitable appendage for measuring glucose levels in vivo. Unfortunately, this technique suffers from two sources of inaccuracy: tissue interference and lack of specificity. Moreover, while the near infrared wavelengths used are easily and economically generated by light emitting diodes (LEDS) and solid state lasers, they are not in a range specifically absorbed by glucose. This lack of "fingerprint" absorbance and interference from tissue pigment and condition render the technique useless for accurate concentration determination but possibly acceptable for trending if stability can be maintained. Samples of prior art patents describing such spectroscopic techniques are described below.

Kaiser describes in Swiss Patent No. 612,271 a technique in which an infrared laser is used as the radiation source for measuring glucose concentration in a measuring cell. The measuring cell consists of an ATR measuring prism which is wetted by the patient's blood and an ATR reference prism which is wetted with a comparison solution. $CO_2$ laser radiation is led through the measuring cell and gathered before striking a signal processing device. A chopper placed before the measuring cell allows two voltages to be obtained corresponding to the signal from the sample and the reference prisms. Due to absorption corresponding to the concentration of the substance measured in the blood, the difference between the resulting voltages is proportional to the concentration. Unfortunately, the infrared laser used by Kaiser has the undesirable side-effect of heating the blood, which may be harmful to the patient, and also does not overcome the effects of tissue absorption. Although Kaiser suggests that heating of the blood may be prevented by using extra-corporeal cuvettes of venous blood and high blood flow rates, Kaiser does not describe a noninvasive technique for measuring glucose concentration which overcomes the effects of tissue absorption or other sources of error which are present in the portion of the infrared spectrum were Kaiser makes his measurements.

March in U.S. Pat. No. 3,958,560 describes a "noninvasive" automatic glucose sensor system which senses the rotation of polarized infrared light which has passed through the cornea of the eye. March's glucose sensor fits over the eyeball between the eyelid and the cornea and measures glucose as a function of the amount of radiation detected at the detector on one side of the patient's cornea. Unfortunately, while such a technique does not require the withdrawal of blood and is thus "noninvasive", the sensor may cause considerable discomfort to the patient because of the need to place it on the patient's eye. A more accurate and less intrusive system is desired.

Hutchinson describes in U.S. Pat. No. 5,009,230 a personal glucose monitor which also uses polarized infrared light to noninvasively detect glucose concentrations in the patient's bloodstream. The amount of rotation imparted on the polarized light beam is measured as it passes through a vascularized portion of the body for measuring the glucose concentration in that portion of the body. Although the monitor described by Hutchinson need not be mounted on the patient's eye, the accuracy of the measurement is limited by the relatively minimal absorption of glucose in the 940-1000 nm range used by Hutchinson.

Dahne et al. in U.S. Pat. No. 4,655,225 describe a spectrophotometric technique for detecting the presence of glucose using specially selected bands in the near infrared region between 1100 and 2500 nm. Dahne et al. found that by applying light at wavelengths in the 1000-2500 nm range acceptable combinations of sufficient penetration depth to reach the tissues of interest with sufficient sensitivity may be obtained for ascertaining glucose concentration variations without the risk of overheating tissues.

Mendelson et al. in U.S. Pat. No. 5,137,023 also found that wavelengths in the near infrared range are useful for noninvasively measuring the concentration of an analyte such as glucose using pulsatile photoplethysmography. In particular, Mendelson et al. describe a glucose measuring instrument which uses the principles of transmission and reflection photoplethysmography, whereby glucose measurement is made by analyzing either the differences or the ratio of two different near infrared radiation sources that are either transmitted through an appendage or reflected from a tissue surface before and after blood volume change occurs in the systolic and diastolic phases of the cardiac cycle. The technique of photoplethysmography can thus be used to adjust the light intensity to account for errors introduced by excessive tissue absorptions. However, despite the assertions by Dahne et al. and Mendelson et al., the wavelengths in the near infrared (below 2500 nm) are not strongly absorbed by glucose yet are susceptible to interference from other compounds in the blood and thus cannot yield sufficiently accurate measurements.

Rosenthal et al. in U.S. Pat. No. 5,028,787 disclose a noninvasive blood glucose monitor which also uses infrared energy in the near infrared range (600-1100 nm) to measure glucose. However, as with the above-mentioned devices, these wavelengths are not in the primary absorption range of glucose and, accordingly, the absorption at these wavelengths is relatively weak. A more accurate glucose measuring technique which monitors glucose absorption in its primary absorption range is desired.

As with other molecules, glucose more readily absorbs infrared light at certain frequencies because of the characteristic and essential invariate absorption wavelengths of its covalent bonds. For example, as described by Hendrickson et al. in *Organic Chemistry*, 3rd Edition, McGraw-Hill Book Company, Chapter 7, Section 7–5, pages 256–264, C—C, C—N, C—O and other single carbon bonds have characteristic absorption wavelengths in the 6.5–15 micron range. Due to the presence of such bonds in glucose, infrared absorption by glucose is particularly distinctive in the far infrared. Despite these characteristics, few have suggested measuring glucose concentration in the middle to far infrared range, likely due to the strong tissue absorption that would attenuate signals in that range.

In one known example of such teachings, Mueller describes in WO 81/00622 a method and device for determining the concentration of metabolites in blood using spectroscopic techniques for wavelengths in the far infrared range. In particular, Mueller teaches the feasibility of measuring glucose in extra-corporeal blood samples using a 9.1 $\mu$m absorption wavelength and a 10.5 $\mu$m reference wavelength for stabilizing the absorption reading. However, Mueller does not describe how such wavelengths maybe used in vivo to measure glucose concentration noninvasively while overcoming the above-mentioned tissue absorption problems. Mueller also does not suggest synchronizing such determinations to the systolic and diastolic phases of the heart for minimizing tissue absorption errors.

Accordingly, it is desired to extend the techniques used in noninvasive pulse oximeters and the like to obtain absorption signals from pulsing arterial blood which can be used for accurate measurements of the concentration of glucose, ethyl alcohol and other blood constituents while overcoming the problems caused by interference from tissues and the like. In particular, a noninvasive blood constituent measuring device is desired which uses long wavelength infrared energy for better absorption characteristics and improved signal to noise ratios while also synchronizing the pulses of long wavelength infrared energy with the cardiac cycle so that very accurate in vivo measurements of the concentrations of such constituents in the arterioles may be made. A method and device for this purpose is described herein.

SUMMARY OF THE INVENTION

The above-mentioned limitations in prior art glucose and other blood constituent measuring devices are overcome by providing an instrument which noninvasively measures the concentration of glucose and other blood constituents in a patient's blood by monitoring the infrared absorption of the blood constituent in the blood at long infrared wavelengths were such blood constituents have strong and readily distinguishable absorption spectra. Preferably, the long wavelength infrared energy is passed through a finger or other vascularized appendage and the measurement is made without injury, venipuncture or inconvenience to the patient.

Since the patient's tissue, water and bone are also strong and variable absorbers of long wavelength infrared energy, the signal to noise ratio is such a system could cause serious errors in the blood constituent concentration measurements. However, potential interference from these sources is overcome in accordance with the present invention by (1) synchronizing the optical transmission measurement with the systolic and diastolic phases of the heart beat and using the resulting expansion and contraction of the arteriole walls to isolate the measurement to only arteriole blood, and (2) making such measurements with a precisely timed "pulse" of relatively high amplitude long wavelength energy.

Long wavelength infrared detectors typically have low responsivities because of the attenuation of the signals by the tissues. These problems are further addressed by the device of the invention by using a high energy infrared source for the blood concentration measurement. However, care must be taken in the application of such high energy infrared energy to the skin of the patient since long wavelength infrared energy from a high energy source may burn or cause patient discomfort. To prevent such problems, only short bursts or "pulses" of infrared energy are sent through the patient's skin. Such "pulses" have a very low duty cycle and low optical bandwidth (due to a relatively narrow source filter) and are synchronized with systole and diastole in accordance with the invention so as to minimize the adverse effects of tissue absorption. Thus, two or more bursts are sent per heart beat so that the patient's skin is not burned and the patient is not otherwise discomforted. An optical plethysmograph or ECG may be used in accordance with the invention to synchronize the bursts of long wavelength infrared energy with the heartbeat.

The present invention thus relates to a noninvasive pulsed infrared spectrophotometer and method thereof which measures the concentration of at least one predetermined blood constituent, such as glucose or ethyl alcohol, in a patient's blood. In accordance with a preferred embodiment of the invention, such a noninvasive pulsed infrared spectrophotometer comprises an infrared source for emitting pulses of infrared light over a broad range of wavelengths of at least 2.0 $\mu$m, where each predetermined constituent readily absorbs pulses of infrared light at one of n wavelengths and minimally absorbs pulses of infrared light at another of the n wavelengths within that range. Infrared light from the infrared source passes through an arterial blood vessel of the patient for absorption by the predetermined constituent. At least one infrared detector then detects light at the n wavelengths which has passed through the arterial blood vessel of the patient and has been selectively absorbed by the predetermined constituent(s) and outputs a detection signal. Synchronizing means are further provided for synchronizing the application of the pulses of infrared light from the infrared source with the systolic and diastolic phases of the cardiac cycle of the patient. Preferably, the synchronizing means comprises a cardiac monitor and means responsive to an output of the cardiac monitor for modulating the pulses of infrared light so that it passes through the arterial blood vessel of the patient only during diastolic and systolic time intervals respectively occurring during the systolic and diastolic phases of the cardiac cycle of the patient. The concentration of the predetermined constituent(s) can then be calculated from the detection signal to provide a concentration indication which is substantially free of tissue absorption errors.

In a preferred embodiment of the invention, the infrared source comprises either a modulated laser or a modulated heated element which emits pulses of infrared light in a wavelength range of 2-20 $\mu$m. In a preferred embodiment of a glucose monitor, the detection wavelength is approximately 9.1 $\mu$m while the reference wavelength is approximately 10.5 $\mu$m. A dichroic filter is also disposed adjacent the infrared source for passing infrared energy in a range of approximately 8-12 $\mu$m and for reflecting infrared energy outside of that range back into the infrared source. In an alternative embodiment of a blood alcohol monitor, the detection wavelength is approximately 3.4 $\mu$m, the reference wavelength is approximately 4.8 $\mu$m and the dichroic filter passes energy in the 3-5 $\mu$m range. So as to minimize the possibility of patient discomfort, the infrared energy is only applied to the patient's skin for approximately 0.1-2 msec during the systolic and diastolic phases of the cardiac cycle of the patient. Preferably, bandpass filters are also disposed between the arterial blood vessel of the patient and the infrared detector(s) for passing infrared light in a narrow passband centered at the detection and reference wavelengths.

In a preferred embodiment of the invention, the modulating means comprises a mechanical shutter disposed between the infrared source and the arterial blood vessel of the patient which is synchronized to the systolic and diastolic phases of the cardiac cycle of the patient so as to allow the infrared light to pass therethrough to the skin of the patient only during the systolic and diastolic phases of the patient's cardiac cycle. Alternatively, the modulating means may comprise means for electrically modulating the pulses of infrared light.

In addition, the cardiac monitor may comprise an electrocardiogram, or preferably, a photoplethysmograph having a pulsed light emitting diode for directing light through a tissue of the patient and a photodetector for detecting the light which has passed through the tissue of the patient. Also, the synchronizing means preferably comprises processing means for processing a detection output of the photodetector to determine the phase of the cardiac cycle and to control opening and closing of the mechanical shutter or electrical modulation of the infrared energy in accordance with the cardiac phase. The processing means may also determine from the detection output of the photodetector when to open the mechanical shutter in the next cardiac cycle so as to make measurements in the systolic and diastolic phases of the next cardiac cycle.

In accordance with a preferred embodiment of the invention, the processing means further determines from the detection output of the photodetector whether systole and diastole actually occurred in the current cardiac cycle at the same time the mechanical shutter was opened in the current cardiac cycle. If so, the detection signal is forwarded to the concentration determining means for determination of the concentration of the predetermined constituent; otherwise, the measurement is ignored. In making such a determination, the processing means preferably repeats the steps of:

(a) for the current cardiac cycle, digitizing the detection output of the photodetector in sampling time intervals of approximately 0.1 to 2.0 msec;

(b) selecting a distinctive feature, such as the dicrotic notch, of the digitized detection output of the photodetector for the current cardiac cycle and labelling the time interval of the distinctive feature as a cardiac cycle start time;

(c) labelling all subsequent time intervals in the current cardiac cycle by incrementing time intervals from the cardiac cycle start time until the distinctive feature is encountered in the next cardiac cycle;

(d) determining a peak in the digitized detection output of the photodetector for the current cardiac cycle and storing a time interval label identifying systole in the current cardiac cycle;

(e) determining a minimum in the digitized detection output of the photodetector for the current cardiac cycle and storing a time interval label identifying diastole in the current cardiac cycle;

(f) during the next cardiac cycle, counting the number of time intervals from a cardiac cycle start time of the next cardiac cycle in accordance with the time interval label identifying diastole for the current cardiac cycle and opening the mechanical shutter for the duration of the diastolic time interval, and then counting a number of time intervals from the diastolic time interval in accordance with the time interval label identifying systole for the current cardiac cycle and opening the mechanical shutter for the duration of the systolic time interval;

(g) when the mechanical shutter is open, recording in memory the detection signal from the infrared detector(s);

(h) repeating steps (a) through (e) for the next cardiac cycle;

(i) determining whether diastole and systole for the next cardiac cycle actually occurred within a predetermined number of time intervals from when the mechanical shutter was opened in step (f); and (j) if it is determined in step (i) that diastole and systole for the next cardiac cycle actually occurred within the predetermined number of time intervals from when the mechanical shutter was opened in step (f), passing the recorded detection signal(s) to the concentration determining means for the calculation of the concentration of the predetermined constituent(s), but if it is determined in step (i) that diastole and systole for the next cardiac cycle did not actually occur within the predetermined number of time intervals from when the mechanical shutter was opened in step (f), erasing the recorded detection signal(s) from memory.

Concentration of the predetermined constituent(s) is calculated by forming a ratio $R = (Sys\ L1 - Dias\ L1)/(Sys\ L2 - Dias\ L2)$, where Sys L1 is a detected systolic phase signal at the detection wavelength, Dias L1 is a detected diastolic phase signal at the detection wavelength, Sys L2 is a detected systolic phase signal at the reference wavelength, and Dias L2 is a detected diastolic phase signal at the reference wavelength, and then solving the following equation:

$$C.C. = C_1 + C_2 * Ln(R) + C_3 * [Ln(R)]^2 + C_4 * [Ln(R)]^3 + C_5 * [Ln(R)]^4,$$

where:

C.C. is the concentration of the predetermined constituent;

$C_1$–$C_5$ are empirically determined calibration coefficients; and

Ln is a natural log function.

The above equation can be generalized for a system using multiple detection wavelengths and one or more reference wavelengths by including cross-product terms in the polynomial as will be shown in more detail below.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings, of which.

DETAILED DESCRIPTION OF THE PRESENTLY PREFERRED EMBODIMENTS

A noninvasive pulsed infrared spectrometer with the above-mentioned beneficial features in accordance with the presently preferred exemplary embodiment of the invention will now be described with reference to FIGS. 1-6. It will be appreciated by those of ordinary skill in the art that by changing the wavelengths of infrared energy applied to the finger and monitored for absorption that other blood constituents such as ethyl alcohol, carbon dioxide, urea, uric acid, lipids, creatinine, peptides, cholesterol and several other metabolites can be measured in accordance with the techniques of the invention. Thus, the glucose monitoring device described herein in the exemplary embodiment is for descriptive purposes only and is not intended in any way to limit to scope of the invention. All questions regarding the scope of the invention may be resolved by referring to the appended claims.

Figure 1:
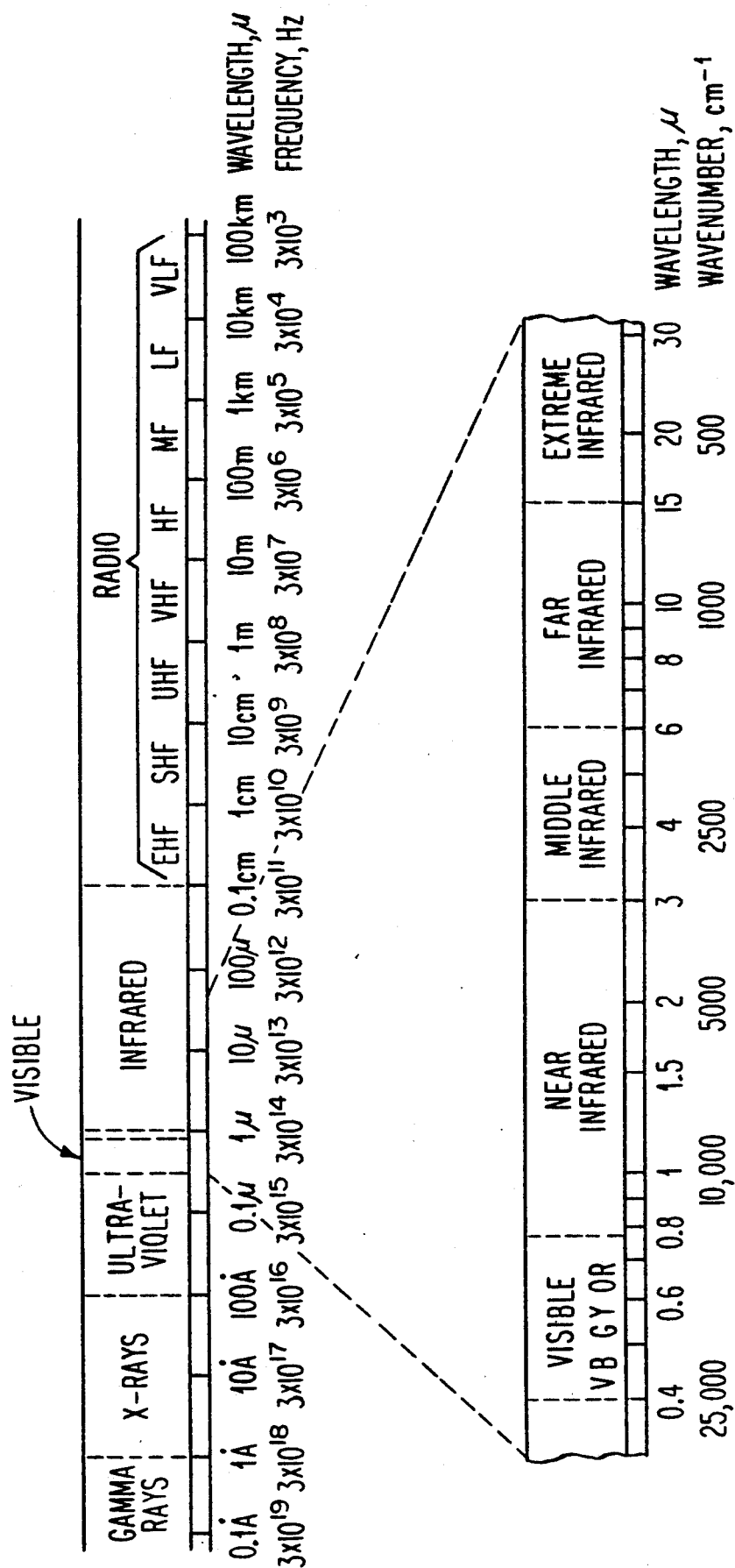
FIG. 1 illustrates the electromagnetic spectrum and, in particular, the portion of the infrared spectrum referred to herein as the near, middle and far infrared.

As known by those skilled in the art, most covalent bonds have characteristics and essentially invariant absorption wavelengths so that the presence of a band in the infrared spectrum illustrated in FIG. 1 indicates the presence of a bond in the molecule while the absence of an absorption peak guarantees the absence of its corresponding bond. Hence, each compound or blood constituent measured in accordance with the techniques of the invention has a characteristic absorption spectrum in the infrared range which may be used to establish one or more detection and reference wavelengths for absorption measurement. Glucose measurement in the far infrared range will be described herein as a presently preferred embodiment, although the present invention has particular utility as a blood alcohol monitor in the middle infrared range.

As shown in FIG. 1, the infrared spectra includes the near infrared (approximately 1 to 3 microns), the middle infrared (approximately 3-6 microns), the far infrared (approximately 6-15 microns), and the extreme infrared (approximately 15-100 microns). As noted above, typical glucose and other blood constituent measuring devices operate in the near infrared region where the absorption of infrared energy by glucose and other blood constituents is relatively low. However, the present inventors have found a technique whereby absorption may be measured in the middle and far infrared regions where glucose and other blood constituents have strong and distinguishable absorption spectra while also minimizing the adverse effects of tissue, water and bone absorption.

Figure 2:
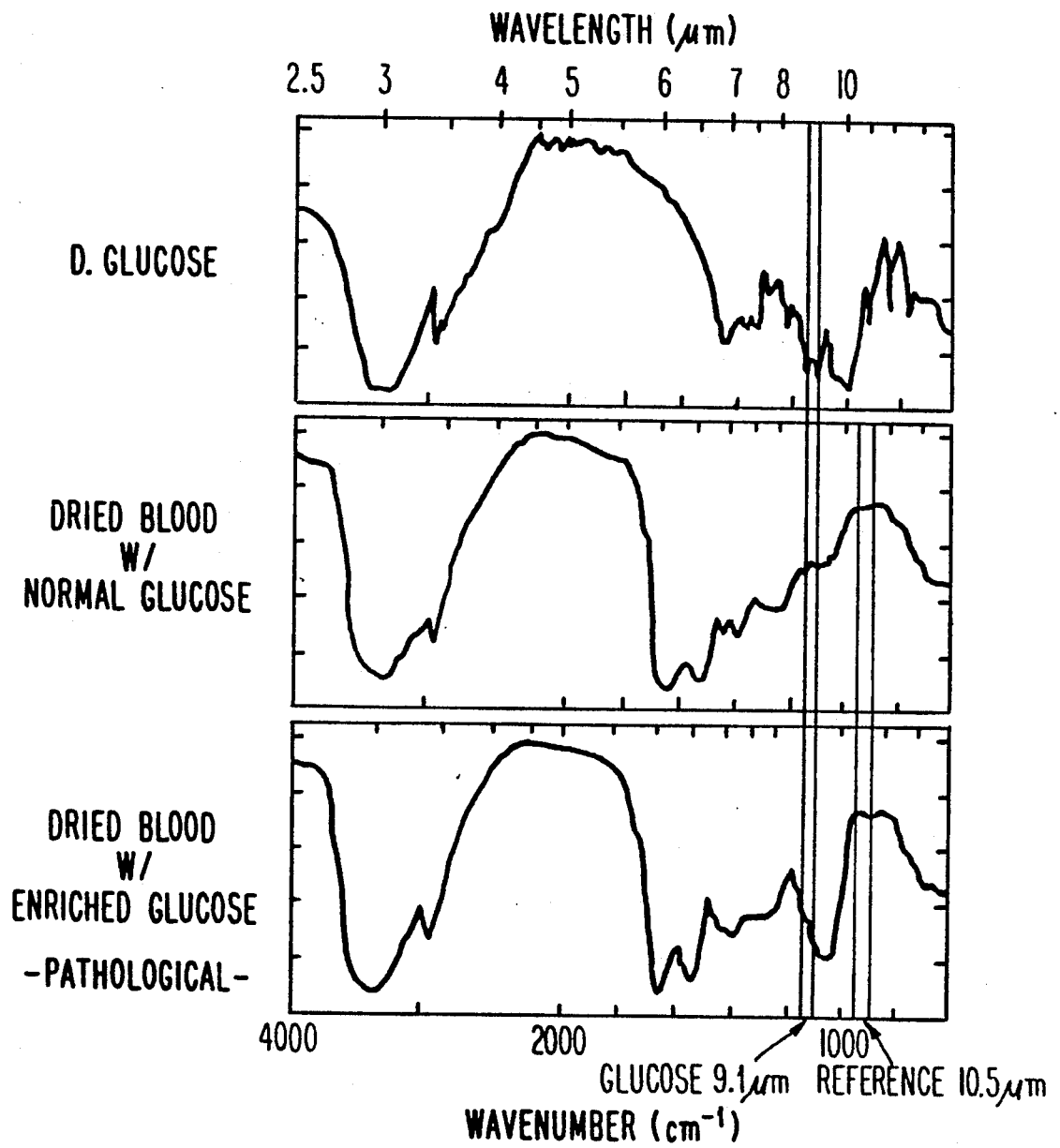
FIG. 2 respectively illustrates the infrared spectra for dextro glucose, dried blood with normal glucose and dried blood with enriched glucose as well as preferred detection and reference wavelengths for measuring glucose concentration in the far infrared.
Figure 3:
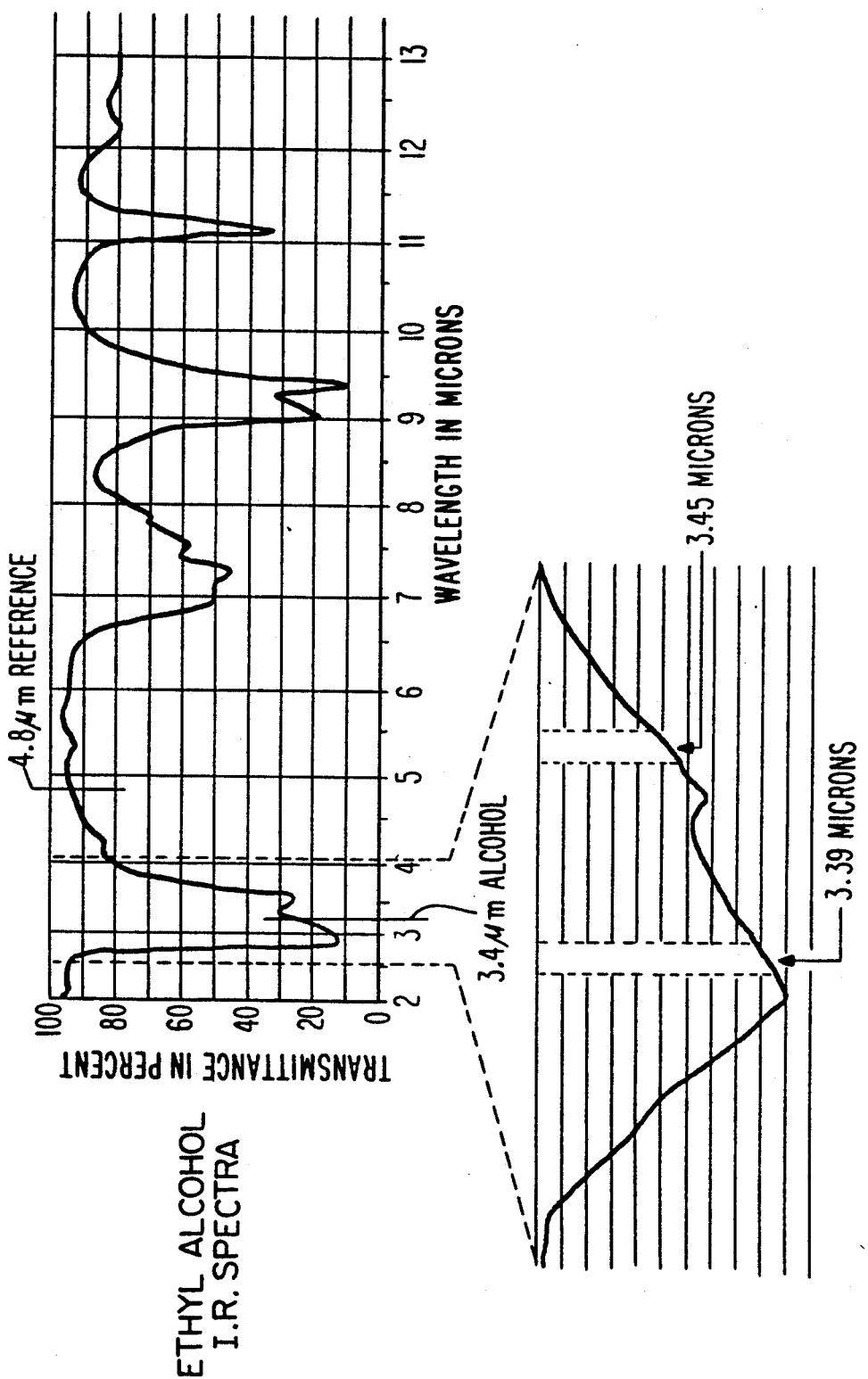
FIG. 3 illustrates the infrared spectra for ethyl alcohol as well as preferred detection and reference wavelengths for measuring the concentration of ethyl alcohol in the middle infrared.

As illustrated in FIG. 2, glucose has strong characteristic spectra in the far infrared above about 6 microns. Indeed, as described by Mueller in the above-changing referenced PCT application, glucose absorption may be measured using a detection wavelength at approximately 9.1 $\mu$m and a reference wavelength at approximately 10.5 $\mu$m. Similarly, as illustrated in FIG. 3, ethyl alcohol has a strong characteristic spectra in the middle infrared (3-4 $\mu$m) and in the far infrared (9-10 $\mu$m). As illustrated, ethyl alcohol concentration may be measured using a detection wavelength of approximately 3.4 microns and a reference wavelength of approximately 4.8 microns using differential absorption calculation techniques.

However, in order to take advantage of the strong and distinguishable absorption spectra in the middle and far infrared regions, an infrared source must be provided which emits high amplitude broadband energy in the middle and far infrared yet can be modulated in such a manner that the skin of the patient would not be burned or harmed. For this reason, in the long wavelength infrared noninvasive blood constituent analyzer in accordance with the invention the long wavelength infrared energy is generated in bursts and applied to the patient during very short time intervals which, as will be described in detail below, are preferably synchronized to systole and diastole. While LEDs and laser diodes have been well suited for generating bursts of energy controlled by an electrical signal in prior art noninvasive short wavelength infrared analyzers, such devices are not capable of generating energy in the middle and long infrared wavelength regions which are primarily absorbed by glucose, ethyl alcohol and other blood constituents measured in accordance with the techniques of the invention. While some expensive solid state lasers can generate bursts of selected long wavelength infrared energy, such lasers are very expensive and the wavelengths generated, while close, are not ideal for measuring glucose.

Accordingly, in accordance with a first aspect of the invention, a novel infrared emitter is constructed of a simple glowing element which may pass infrared energy though an appendage of a patient such as finger without discomfort. Preferably, the glowing element comprises a glowing "heater" or infrared source which, in a preferred embodiment, is constructed using 5-10 turns of KANTHAL ™ heater wire operated at approximately 20 watts. Alternatively, an infrared laser may be used. Such a source preferably emits infrared radiation over a wide range including the 9-11 $\mu$m band used for analyzing glucose in accordance with the techniques described herein.

Figure 4:
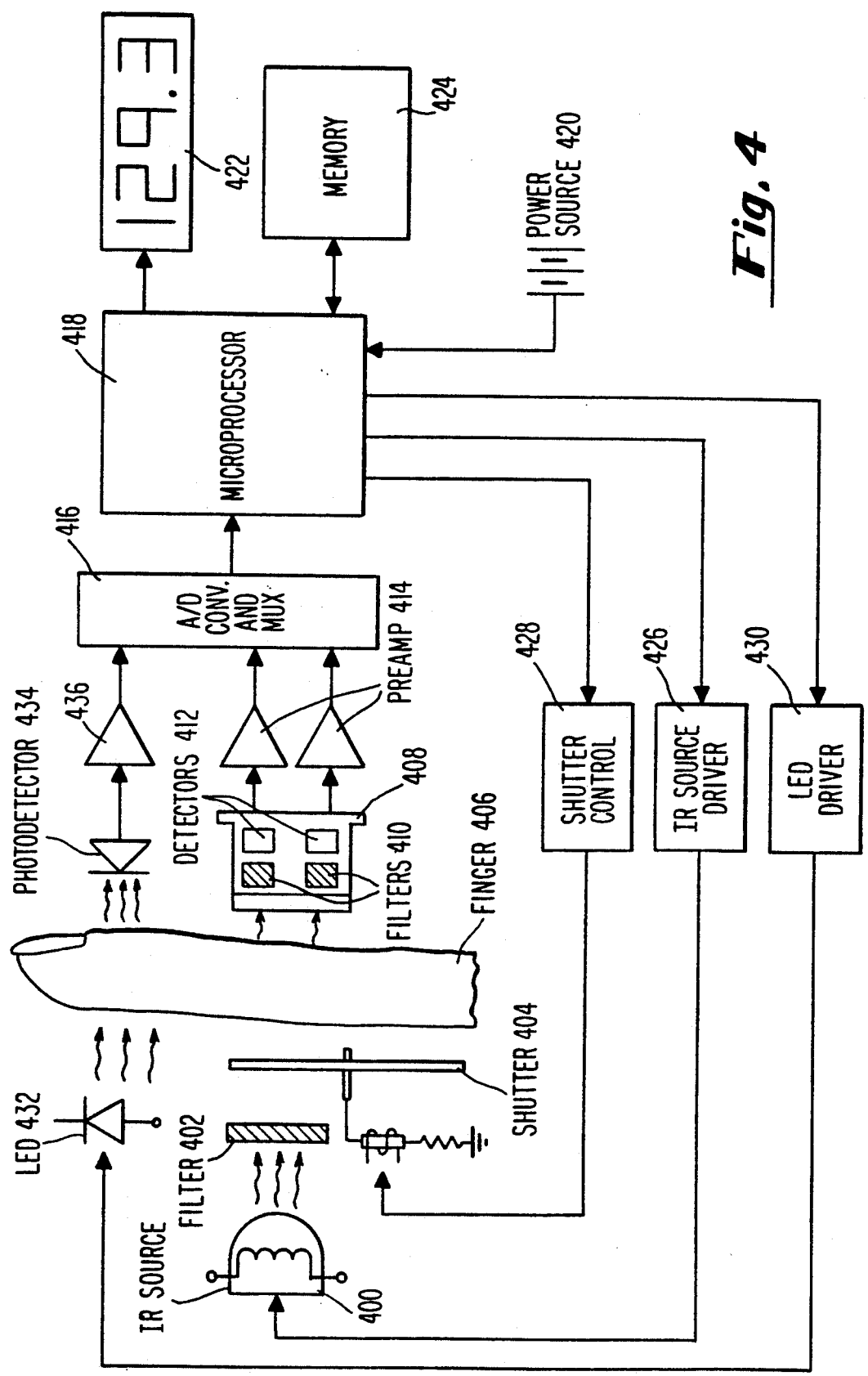
FIG. 4 schematically illustrates a preferred embodiment of a noninvasive pulsed infrared spectrophotometer in accordance with the invention.
Figure 5:
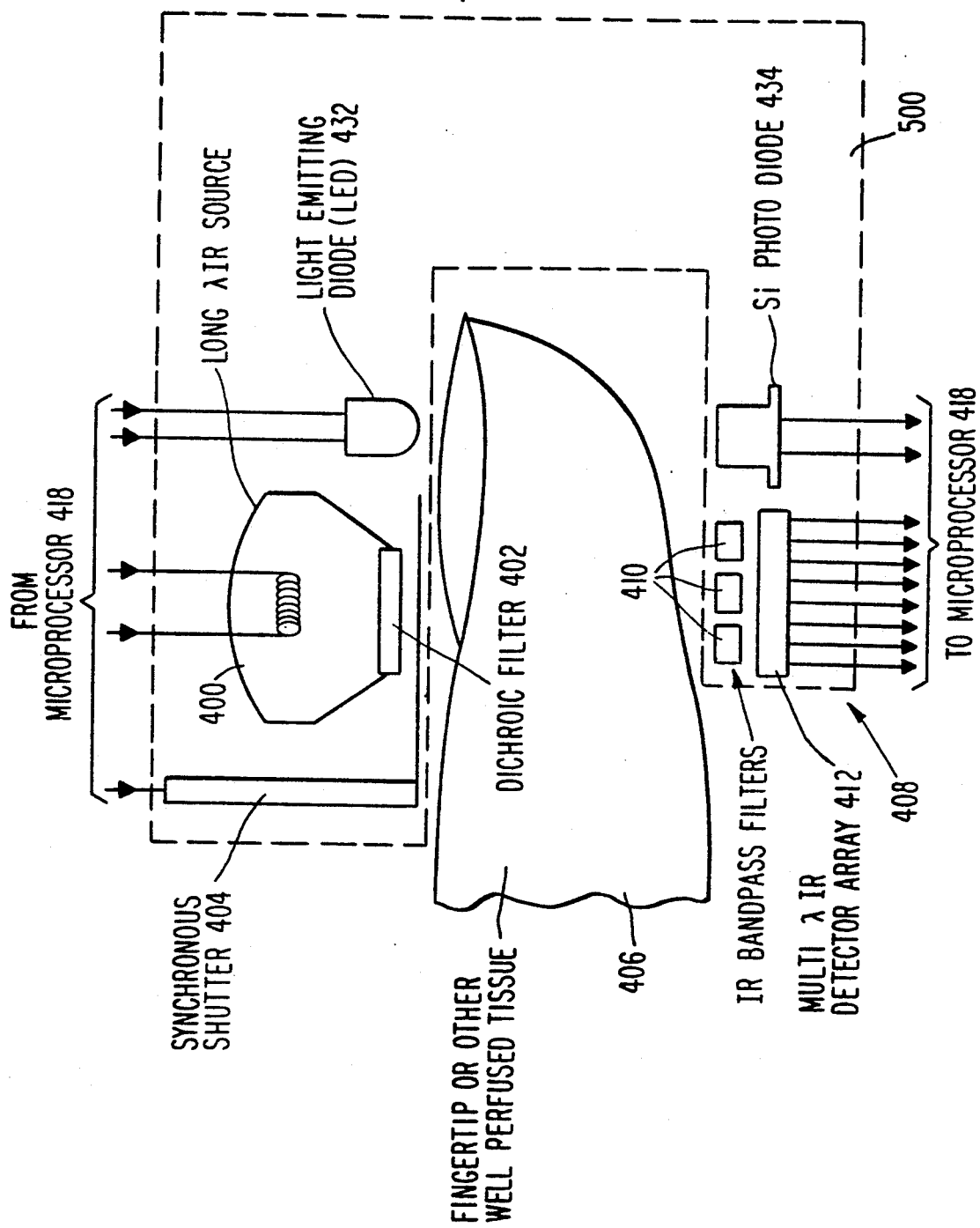
FIG. 5 illustrates an enlarged view of the transmission and detection circuitry in the embodiment of FIG. 4 as well as a photoplethysmograph for detecting systole and diastole in accordance with a preferred embodiment of the invention.

A preferred embodiment of the noninvasive pulsed infrared spectrophotometer in accordance with the invention is illustrated in FIGS. 4 and 5. As shown in these figures, infrared source 400 emits broadband infrared energy in a wavelength range of approximately 2-20 $\mu$m which includes the 9-11 $\mu$m band used for analyzing glucose in the preferred embodiment. Preferably, a focusing mirror is also provided behind the infrared source 400 for concentrating the output energy. Next to the infrared source 400 is a dichroic filter 402 which passes energy in the 8-12 $\mu$m band and reflects other wavelengths back into the infrared source 400 in the preferred embodiment. The dichroic filter 402 limits the amount of power delivered from the infrared source 400 by limiting the wavelength range to the desired range while allowing the full energy of the desired wavelengths to pass. Dichroic filter 402 in the preferred embodiment is manufactured by optical Coating Laboratory, Inc. (OCLI).

As illustrated in FIGS. 4 and 5, an optical shutter 404 is preferably located between the dichroic filter 402 and the patient's finger or other perfused tissue 406. Shutter 404 remains closed for most of the cardiac cycle so as to block the filtered long wavelength infrared energy from infrared source 400 from reaching the patient's finger 406 and thereby preventing patient discomfort from heating. In the preferred embodiment, shutter 404 is a model LS2 mechanical shutter manufactured by Uniblitz, Inc. which is driven by the Uniblitz Model D880 shutter control circuit. Shutter 404 is preferably synchronized to the cardiac cycle in accordance with techniques to be described in more detail below.

In the preferred embodiment, the flow of infrared energy from the infrared source 400 into the patient's finger 406 is optimally controlled by only opening shutter 404 for a few milliseconds (typically approximately 2 milliseconds) twice each heart beat, which has a typical duration of approximately 750 milliseconds. In this manner, the duty cycle of the infrared energy applied to the appendage is kept very low so as to allow the delivery of relatively high amplitude bursts of energy into the patient's tissue 406 so that it penetrates the tissue 406 while keeping the overall energy delivered very low so that no discomfort is experienced. Alternatively, the infrared energy from the infrared source 400 may be electrically modulated using techniques known by those skilled in the art so that short bursts of infrared energy may be passed through the arteriole blood vessels of the tissue 406 during the prescribed time intervals in the cardiac cycle. As illustrated by broken line in FIG. 5, the infrared source 400, dichroic filter 402 and shutter 404 form an infrared signal source which may be placed in a housing 500 for accepting a patient's finger 406 and the like.

The long wavelength infrared energy from infrared source 400 which passes through the patient's finger 406 is detected by a multi-wavelength infrared detector 408 comprised of two or more infrared bandpass filters 410 and two or more infrared detectors 412. Filters 410 may be custom manufactured for this instrument by a manufacturer such as OCLI so that they have narrow passbands about the detection and reference wavelengths. For example, in the glucose embodiment described herein, the pass band for the analytical filter of filters 410 is 9.1 $\mu$m with a half power bandwidth of 0.2 $\mu$m and for the reference filter of filters 410 is 10.5 $\mu$m with a half power bandwidth of 0.2 $\mu$m. The long wavelength infrared detectors 412 used in the preferred embodiment are preferably of a pyroelectric type such as model DTG-2 provided by Infrared Associates, Inc. However, those skilled in the art will appreciate that thermopile detectors such as those model DR34 from Dexter Research, Inc. or other types having responses in the 8-12 $\mu$m range may also be used as well.

The electrical signals generated by the detectors 412 are preferably amplified by preamplifiers 414 and then converted into digital signals by analog to digital converter/multiplexer 416. The resulting digital signals are then selectively applied to microprocessor 418 for calculation of the concentration of glucose or other blood constituent which is being measured.

Microprocessor 418 receives energy from an AC or DC power source 420 which preferably permits the invention to be miniaturized for use in a hand-held monitor. The calculated concentration is then displayed on display 422 so that the user may readily ascertain his or her glucose level, ethyl alcohol level, and the like. Microprocessor 418 preferably further includes memory 424 for storing sequences of such measurements so that averaging and trending and the like may be conducted.

The ability to generate high energy bursts of infrared energy provides a means for measuring the long wavelength infrared absorption of the tissue and blood in accordance with the invention. To selectively measure only the blood absorption and thus glucose in the blood, one pulse is precisely timed to measure the finger's infrared light transmission when the arterioles are full of blood and enlarged during systole, while a second pulse is precisely timed to measure the finger's infrared light transmission when the arterioles are devoid of blood and shrunken during diastole. Since only the arterioles expand and contract with the heartbeat, the tissue and venous blood remain constant throughout the cardiac cycle. This expansion and resultant increase in optical path length through the arterial blood cyclically attenuates the resulting signal. Hence, subtraction of the diastolic signal from the systolic signal will yield a signal in which only incremental infrared absorption of the arteriole blood (and hence glucose) is represented.

As noted above, conventional pulse oximeters as well as the near infrared glucose analyzer described by Mendelson emit pulses (typically one millisecond long) thousands of times per heart beat and then reconstruct the signals in a processor after the heart beat is over. Then, the samples that corresponded to the peak signal (diastole) and the minimum signal (systole) are selected and used for further computation. However, when working with the longer wavelength infrared energy and higher power source of the present invention, continuous bursts of infrared pulses may not be applied to the patient's skin without causing burns or discomfort to the patient. Accordingly, the present invention uses only 2 pulses per cardiac cycle, one during systole and the other diastole. The timing of the application of these bursts of energy is determined ahead of time by synchronizing the shutter 404 and hence the infrared source 400 to the cardiac cycle.

Systole and diastole of the cardiac cycle is determined in the preferred embodiment using a plethysmograph signal obtained from a short wavelength pulsed infrared LED 432 driven by LED driver 430 and microprocessor 418 by a silicon photodetector 434 which obtains a basis for predicting the cardiac cycle. The output of photodetector 434 is applied to a preamplifier 436, converted to digital form by analog to digital converter 416 and then selectivity applied to microprocessor 418 for predicting the occurrences of systole and diastole in the next cardiac cycle on the bases of the occurrence of systole and diastole in the current cardiac cycle. In particular, using the property of the heart that the cardiac cycle does not change much from beat to beat, a prediction of where in the next cardiac cycle systole and diastole will occur is made based upon the output of photodetector 434. This prediction is then used to control shutter 404 via shutter control 428 to trigger the long wavelength infrared pulses in the next cardiac cycle. Simultaneously with launching and detecting long wavelength infrared pulses using shutter 404, the plethysmograph signal from photodetector 434 for the current cardiac cycle is processed to see if systole and diastole did indeed occur at the prescribed point in current cardiac cycle. If they did, the long wavelength data detected by detectors 412 is saved in memory 424 and used by microprocessor 418 to calculate glucose concentration. However, if systole and diastole did not occur at the prescribed point in the cycle, the measured data is discarded. In this manner, even if the cardiac cycle did change rapidly from one cycle to the next and the prediction was not valid, erroneous glucose concentrations are not computed. After collection of a sufficient quantity of "good" long wavelength infrared pulses, the final glucose concentration is computed by microprocessor 418 and displayed on display 422. Of course, several measurements may be stored in memory 424 and then averaged to obtain an acceptable reading.

The photoplethysmograph used in a preferred embodiment of the invention operates as follows. An LED 432 forms a visible or near infrared light source which is pulsed by microprocessor 418 and LED driver circuit 430. The LED signal is not passed through the shutter 404 and is instead passed directly through the finger 406 and detected by a silicon photodetector 434. Synchronous demodulation electronics in preamplifier 436 convert the output of silicon detector 434 into a useful plethysmograph signal which is processed by microprocessor 418 as will be described below. LED 432, photodetector 434 and preamplifier circuit 436 thus together comprise an optical plethysmograph which is used by the microprocessor 418 to determine the phase of the cardiac cycle. Using this information, microprocessor 418 controls the opening of the long wavelength infrared shutter 404 by timing it to coincide with systole and diastole when the arterioles are swollen and relatively empty of blood, respectively.

Of course, other techniques for monitoring the cardiac cycle maybe used. For example, the cardiac monitor may utilize an electrocardiogram for synchronizing to a characteristic feature of the electrocardiogram. In addition, the infrared source 400 may be electrically modulated by microprocessor 418 so that light passes through arteriole blood vessels of the patient only during the diastolic and systolic time intervals.

Figure 6:
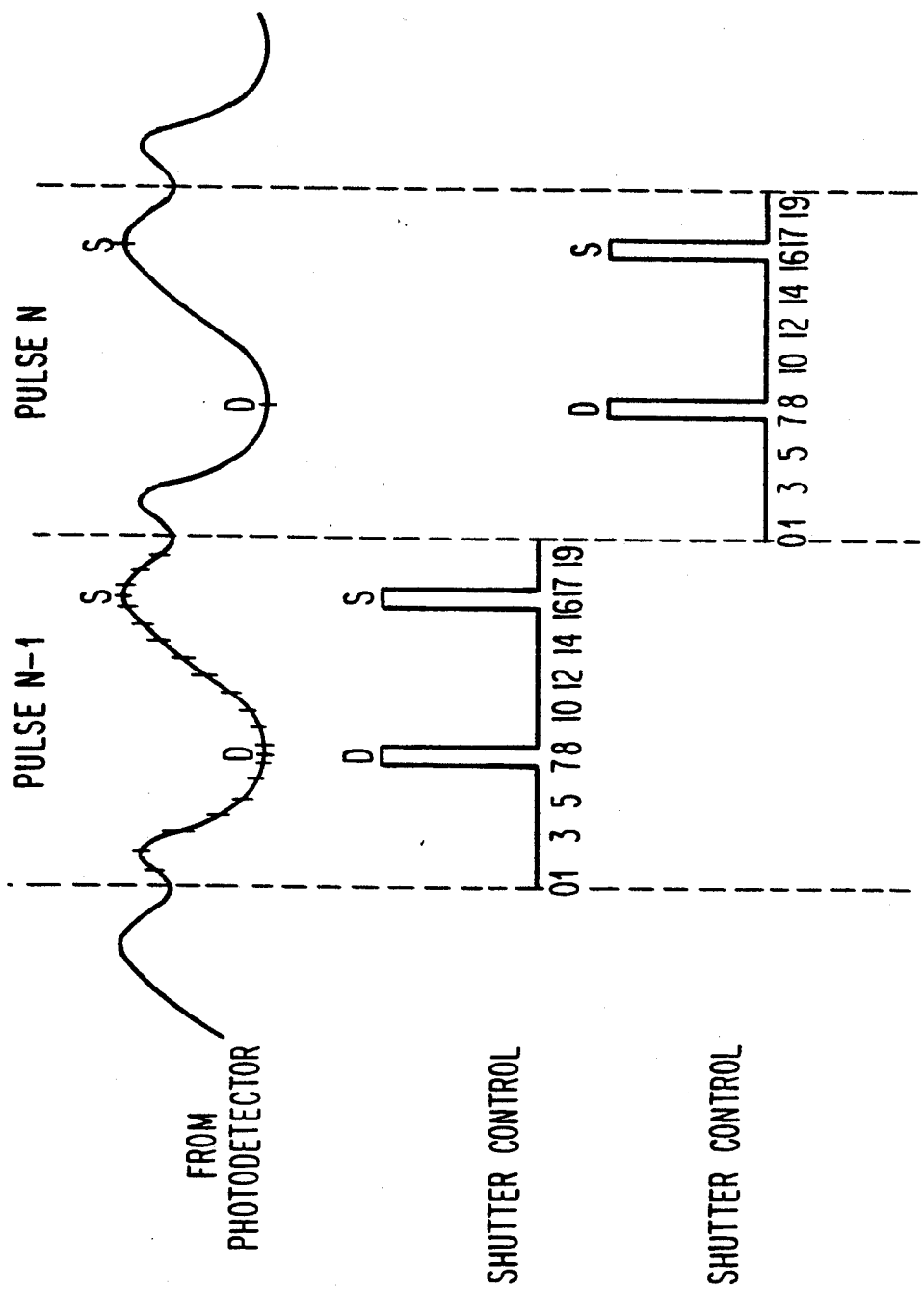
FIG. 6 illustrates the preferred technique for synchronizing the application of infrared energy with systole and diastole.

In accordance with a preferred embodiment of the invention, microprocessor 418 processes the plethysmograph signal from photodetector 434 in order to determine systole and diastole in the next cardiac cycle as follows:

1. A conventional plethysmograph signal is obtained by photodetector 434, digitized by analog to digital converter 416 and recorded in memory 424 as pulse N−1. As illustrated in FIG. 6, this is accomplished by dividing the plethysmograph signal N−1 into sampling intervals having durations of approximately 0.1 to 2 msec. In a preferred embodiment, the plethysmograph signal from photodetector 434 is sampled by analog to digital converter 416 every 1 msec.

2. As further illustrated in FIG. 6, a characteristic feature of the cardiac cycle waveform is selected for purpose of synchronization. In a preferred embodiment, the dicrotic notch, which, as shown, is a feature on the waveform of the cardiac cycle where a distinctive dip occurs as a result of the closing of the ventricular valves in the heart, is selected and labelled as time zero for cycle N−1. All other 1 msec intervals occurring after the dicrotic notch are labelled as one, two, three, etc. until the next dicrotic notch for the cycle N is found.

3. The waveform N−1 is then examined to find the peak signal point (systole) and the interval number (i.e., the number of intervals or msec from the dicrotic notch) is stored.

4. The waveform N−1 is then examined to find the minimum signal point (diastole) and the interval number is also stored.

5. In cardiac cycle N, running in real time, the dicrotic notch is again identified. The interval number stored in step 4 for pulse N−1 is then counted from the dicrotic notch to determine the time interval anticipated to correspond to diastole for cycle N. The long wavelength infrared shutter 404 is then opened for approximately 2 milliseconds for application of the long wavelength infrared energy from infrared source 400. At the end of this 2 millisecond interval, the appropriate number of intervals is counted to determine the time interval anticipated to correspond to systole in cycle N. The long wavelength infrared shutter 404 is then opened again for approximately 2 milliseconds for application of the long wavelength infrared energy from infrared source 400.

6. When the long wavelength infrared shutter 404 is open during cycle N, the absorption signals developed by the infrared detectors 412 are digitized by analog to digital converter 416 and stored in memory 424 or another temporary register of microprocessor 418.

7. In cycle N, the infrared LED plethysmograph signal is again recorded and examined. If is determined that systole and diastole occurred within approximately +/−2 msec of where they were predicted to have occurred during analysis of pulse N−1, the long wavelength infrared data stored in memory 424 or some other temporary register is then passed to the glucose processing algorithm of microprocessor 418 for calculation of the glucose concentration. However, if systole and diastole did not occur within +/−2 msec of where they were predicted to have occurred in cycle N−1, the stored values are erased from memory 424.

8. Steps 1–7 are then repeated until a number of usable measurements have been made. The measurements may then be averaged or the highest and lowest values thrown out so that an accurate calculation of concentration may be made by microprocessor 418 and displayed on display device 422.

As just noted, FIG. 6 illustrates the calculation of diastole and systole for the current cardiac cycle (pulse N−1) and the next cardiac cycle (pulse N). As illustrated, samples are taken beginning with the dicrotic notch for pulse N−1 and the intervals during which diastole (interval 8) and systole (interval 17) occur are determined. Shutter 404 is then controlled to open during interval 8 and interval 17 for the next cardiac cycle as illustrated. The plethysmograph signal for the next cardiac cycle is then compared to the time interval during which the shutter 404 was opened to see if the calculation was acceptably accurate. If so, the measured data is passed to the glucose concentration algorithm as previously described.

Measurement of the infrared detection signal is synchronized with the heart beat as just described in order to remove the effects of tissue and other "non pulsating" interferants sometimes referred to as patient variations. However, heart beats are not the same every time and vary from individual to individual. In addition, infrared sources sometimes drift in their output intensity. These variations present a challenge to calibration of an instrument in accordance with the invention. Accordingly, in order to normalize the absorption readings and overcome the requirement for individual calibrations, at least two long infrared wavelengths are measured simultaneously for each burst of infrared energy from infrared source 400 which is applied during diastole and systole as just described. As described above, for glucose the analytical wavelength specifically absorbed by glucose is preferably in the range of approximately 9.1 $\mu$m, while the reference wavelength is preferably in the range of approximately 10.5 $\mu$m, which is not absorbed by glucose. Generally, glucose concentration is determined by forming a ratio between the systolic and diastolic difference signals measured at 9.1 $\mu$m versus those measured at 10.5 $\mu$m. More than one reference and analytical wavelength may be used so that multiple ratios are formed. The resulting arrays of numbers are then operated upon by empirically determined calibration coefficients. The resulting computation yields the concentration of glucose in the patient's arterial blood.

The general form of the mathematics used by microprocessor 418 for calculating the concentration of a blood component such as glucose from absorption signals generated at two or more wavelengths in accordance with the techniques of the invention will now be described.

In general, for a system of n+1 detection wavelengths for detecting n blood constituents such as glucose, alcohol and the like, where the systolic phase signal at wavelength n is SYS LN and the diastolic phase signal at wavelength n is DIAS LN, the concentration of the blood component (such as glucose) being measured can be computed as a mathematical function of SYS LN and DIAS LN. For example, the component concentration (C.C.) may be represented as:

$$C.C. = Fn(SYS\ LN,\ DIAS\ LN).$$

For a system using multiple (at least two) wavelengths where L1-LN are analytical wavelengths and LR is one or more reference wavelengths, then:

$$R_N = (SYS\ LN - DIAS\ LN)/(SYS\ LR - DIAS\ LR) \qquad EQ.(1)$$

Of course, other mathematical forms of the ratio R may be used, but in general, $R_N = FN(LN, LR)$.

The concentration of each blood constituent is then a function of each ratio R for that constituent. For example, glucose concentration (G.C.) may be calculated from a polynomial equation of order p for a single detection and a single reference wavelength as:

$$G.C = C_1 + C_2*Ln(R) + C_3*[Ln(R)]^2 + C_4*[Ln(R)]^3 + C_5*[Ln(R)]^4, \qquad EQ.(2)$$

where $C_1$-$C_5$ are calibration constants, Ln is the natural log function and p=4. However, when plural detection wavelengths and/or plural reference wavelengths are used, cross-product terms would be added, resulting in the following generalized equation:

$$C.C._n = B + \sum_{x=1}^{x=(m-1)} \left[ \sum_{y=1}^{y=p} C_{x,y}*[Ln(R_x)]^y \right] + \sum_{z=1}^{z=p} D_z*[Ln(R_1)*Ln(R_2) \ldots *Ln(R_n)]^z \qquad EQ.\ (3)$$

where B, $C_{x,y}$, and $D_z$ are calibration constants, m is the total number of analytical and reference wavelengths (m> =(n+1)) and Ln in the natural log function. Of course, other equations besides a polynomial equation may be used by those skilled in the art to calculate the concentration of the respective blood constituents.

As noted above, the preferred embodiment of the invention described herein is specifically designed to monitor glucose which absorbs selectively near 9.1 μm. However, those skilled in the art will appreciate that by changing the wavelengths of infrared energy detected other bloodstream constituents such as carbon dioxide which absorbs near 4.3 μm, ethyl alcohol which absorbs near approximately 3.4 microns, urea, uric acid, lipids, creatinine, peptides, cholesterol (all absorbing in the 5-10 μm band) and several other metabolites can be measured. Also, the dialysis fluid of kidney patients may be monitored using the techniques of the invention.

The invention herein described offers both absolute accuracy and noninvasive measurement, thereby making it acceptable for use by anyone needing to measure or monitor his or her blood glucose level, ethyl alcohol level or other blood constituents levels. Use of long wavelength infrared absorbance measurements provide signals at the exact wavelengths absorbed specifically and strongly by glucose or some other blood constituent, while use of pulsed and cardiac synchronized infrared energy bursts removes interference effects caused by tissue absorption yet provides for a high energy infrared signal without patient discomfort.

Although an exemplary embodiment of the invention has been described in detail above, those skilled in the art will readily appreciate the many additional modifications are possible in the exemplary embodiment without materially departing from the novel teachings and advantages of the invention. For example, the present invention may be used to measure other blood constituents such as those mentioned herein by selecting one or more analytical wavelengths and one or more reference wavelengths using techniques known to those skilled in the art. Accordingly, these and all such modifications are intended to be included within the scope of the invention as defined in the following claims.

We claim:

1. A noninvasive pulsed infrared spectrophotometer for measuring the concentration of at least one predetermined constituent of a patient's blood, comprising:

an infrared source which emits broadband pulses of infrared light including n different wavelengths of at least 2.0 μm, said pulses of infrared light containing energy at each of said n wavelengths being differentially absorbed by said at least one predetermined constituent whereby each predetermined constituent readily absorbs pulses of infrared light at one of said n wavelengths and minimally absorbs pulses of infrared light at another of said n wavelengths, and which directs said pulses of infrared light through an arterial blood vessel of the patient;

at least one infrared detector which detects light at said n wavelengths which has passed through said arterial blood vessel of the patient and has been selectively absorbed by said at least one predetermined constituent and which outputs at least one detection signal;

synchronizing means for synchronizing the application of said pulses of infrared light from said infrared source to said arterial blood vessel of the patient with the systolic and diastolic phases of a cardiac cycle of the patient, said synchronizing means including a cardiac monitor and means responsive to an output of said cardiac monitor for modulating said pulses of infrared light so that said infrared light passes through said arterial blood vessel of the patient only during diastolic and systolic time intervals respectively occurring during the systolic and diastolic phases of said cardiac cycle of the patient; and means for determining the concentration of said at least one predetermined constituent of the patient's blood from said at least one detection signal.

2. A spectrophotometer as in claim 1, wherein said infrared source comprises one of a modulated laser and a modulated heated element which emits pulses of infrared light in a wavelength range of 2-20 μm.

3. A spectrophotometer as in claim 2, further comprising a dichroic filter adjacent said infrared source which passes infrared energy in a range of approximately 8-12 μm and reflects infrared energy outside of said range back into said infrared source.

4. A spectrophotometer as in claim 2, wherein said diastolic and systolic time intervals each have durations of approximately 0.1-2 msec during the systolic and diastolic phases of said cardiac cycle of the patient.

5. A spectrophotometer as in claim 2, wherein said at least one predetermined constituent includes glucose, said one wavelength is approximately 9.1 μm and said another wavelength is approximately 10.5 μm.

6. A spectrophotometer as in claim 5, further comprising a first bandpass filter disposed between the arterial blood vessel of the patient and said at least one infrared detector, said first bandpass filter passing infrared light in a narrow passband centered at approximately 9.1 μm, and a second bandpass filter disposed between the arterial blood vessel of the patient and said at least one infrared detector, said second bandpass filter passing infrared light in a narrow passband centered at approximately 10.5 μm.

7. A spectrophotometer as in claim 2, wherein said at least one predetermined constituent includes ethyl alcohol, said one wavelength is approximately 3.4 μm and said another wavelength is approximately 4.8 μm.

8. A spectrophotometer as in claim 7, further comprising a first bandpass filter disposed between the arterial blood vessel of the patient and said at least one infrared detector, said first bandpass filter passing infrared light in a narrow passband centered at approximately 3.4 μm, and a second bandpass filter disposed between the arterial blood vessel of the patient and said at least one infrared detector, said second bandpass filter passing infrared light in a narrow passband centered at approximately 4.8 μm.

9. A spectrophotometer as in claim 1, wherein said modulating means comprises a mechanical shutter disposed between said infrared source and said arterial blood vessel of the patient which is synchronized to said systolic and diastolic phases of said cardiac cycle of the patient so as to allow said infrared light to pass therethrough from said infrared source to the skin of the patient only during said systolic and diastolic time intervals respectively occurring during the systolic and diastolic phases of said cardiac cycle of the patient.

10. A spectrophotometer as in claim 9, wherein said cardiac monitor comprises a photoplethysmograph having a pulsed light emitting diode which directs light through a tissue of the patient and a photodetector which detects the light which has passed through said tissue of the patient, and said synchronizing means further comprises processing means for processing a detection output of said photodetector to determine a phase of said cardiac cycle and to control opening and closing of said mechanical shutter in accordance with said phase.

11. A spectrophotometer as in claim 10, wherein said processing means determines from said detection output of said photodetector when to open said mechanical shutter in a next cardiac cycle in accordance with the systolic and diastolic phases detected in a current cardiac cycle.

12. A spectrophotometer as in claim 11, wherein said processing means further determines from said detection output of said photodetector whether systole and diastole actually occurred in the current cardiac cycle at the same time said mechanical shutter was opened in the current cardiac cycle, and if said, forwarding said at least one detection signal to said concentration determining means for determination of the concentration of said at least one predetermined constituent.

13. A spectrophotometer as in claim 12, wherein said processing means includes a memory, said processing means repeating the steps of:
(a) for the current cardiac cycle, digitizing said detection output of said photodetector in sampling time intervals;
(b) selecting a distinctive feature of the digitized detection output of said photodetector for the current cardiac cycle and labelling a time interval of said distinctive feature as a cardiac cycle start time;
(c) labelling all subsequent time intervals in the current cardiac cycle by incrementing time intervals from said cardiac cycle start time until said distinctive feature is encountered in the next cardiac cycle;
(d) determining a peak in said digitized detection output of said photodetector for the current cardiac cycle and storing a time interval label identifying systole in the current cardiac cycle;
(e) determining a minimum in said digitized detection output of said photodetector for the current cardiac cycle and storing a time interval label identifying diastole in the current cardiac cycle;
(f) during the next cardiac cycle, counting a number of time intervals from a cardiac cycle start time of the next cardiac cycle in accordance with the time interval label identifying diastole for the current cardiac cycle and opening said mechanical shutter for a duration of said diastolic time interval, and then counting a number of time intervals from said diastolic time interval in accordance with the time interval label identifying systole for the current cardiac cycle and opening said mechanical shutter for a duration of said systolic time interval;
(g) when said mechanical shutter is open, recording in said memory said at least one detection signal from said at least one infrared detector;
(h) repeating steps (a) through (e) for the next cardiac cycle;
(i) determining whether diastole and systole for the next cardiac cycle actually occurred within a predetermined number of time intervals from when said mechanical shutter was opened in step (f); and
(j) if it is determined in step (i) that diastole and systole for the next cardiac cycle actually occurred within said predetermined number of time intervals from when said mechanical shutter was opened in step (f), passing said recorded at least one detection signal to said concentration determining means for the calculation of the concentration of said at least one predetermined constituent, but if it is determined in step (i) that diastole and systole for the next cardiac cycle did not actually occur within said predetermined number of time intervals from when said mechanical shutter was opened in step (f), erasing said recorded at least one detection signal from said memory.

14. A spectrophotometer as in claim 13, wherein said distinctive feature of the digitized detection output of said photodetector for the current cardiac cycle is a dicrotic notch of the current cardiac cycle.

15. A spectrophotometer as in claim 13, wherein each sampling time interval has a duration of approximately 0.1 to 2.0 ms.

16. A spectrophotometer as in claim 1, wherein said cardiac monitor comprises an electrocardiogram.

17. A spectrophotometer as in claim 1, wherein said modulating means comprises means for electrically modulating said pulses of infrared light so that said infrared light passes through said arterial blood vessel of the patient only during said diastolic and systolic time intervals.

18. A spectrophotometer as in claim 1, wherein said concentration determining means forms a ratio $R_1 = (\text{Sys } L1 - \text{Dias } L1)/(\text{Sys } L2 - \text{Dias } L2)$, where Sys L1 is a detected systolic phase signal at said one wavelength, Dias L1 is a detected diastolic phase signal at said one wavelength, Sys L2 is a detected systolic phase signal at said another wavelength, and Dias L2 is a detected diastolic phase signal at said another wavelength.

19. A spectrophotometer as in claim 18, wherein said concentration determining means calculates the concentration of said at least one predetermined constituent (n) of the patient's blood in accordance with the following equation:

$$C.C._n = B + \sum_{x=1}^{x=(m-1)} \left[ \sum_{y=1}^{y=p} C_{x,y}*[\text{Ln}(R_x)]^y \right] + \sum_{z=1}^{z=p} D_z*[\text{Ln}(R_1)*\text{Ln}(R_2)\ldots*\text{Ln}(R_n)]^z \quad [\text{EQ. (3)}]$$

where:
$C.C._n$ is the concentration of said at least one predetermined constituent n;
$B$, $C_{x,y}$ and $D_z$ are empirically determined calibration coefficients; m is the number of detection and reference wavelengths used;
p is the highest order of polynomial used; and Ln is a natural log function.

20. A method of noninvasively measuring the concentration of at least one predetermined constituent of a patient's blood, comprising the steps of:
emitting pulses of infrared light at n different wavelengths of at least 2.0 μm, pulses of infrared light at each of said n wavelengths being differentially absorbed by said at least one predetermined constituent, each predetermined constituent readily absorbing pulses of infrared light at one of said n wavelengths and minimally absorbing pulses of infrared light at another of said n wavelengths, and directing said pulses of infrared light through an arterial blood vessel of the patient;
detecting light at said n wavelengths which has passed through said blood vessel of the patient and has been selectively absorbed by said at least one predetermined constituent and outputting at least one detection signal;
synchronizing the direction of said pulses of infrared light through said arterial blood vessel of the patient with the systolic and diastolic phases of a cardiac cycle of the patient; and
determining the concentration of said at least one predetermined constituent of the patient's blood from said at least one detection signal.

21. A method as in claim 20, wherein said synchronizing step includes the step of modulating said pulses of infrared light so that said infrared light passes through said arterial blood vessel of the patient only during diastolic and systolic time intervals respectively occurring during the systolic and diastolic phases of said cardiac cycle of the patient.

22. A method as in claim 21, wherein said synchronizing step includes the steps of directing light through a tissue of the patient, detecting the light which has passed through said tissue of the patient, and processing a detection output of said light detecting step to determine the phase of said cardiac cycle and to control modulation of said pulses of infrared light in said modulating step.

23. A method as in claim 22, wherein said synchronizing step includes repeating the steps of:
(a) for a current cardiac cycle, digitizing said detection output of said infrared light detecting step in sampling time intervals;
(b) selecting a distinctive feature of the digitized detection output of said digitizing step for the current cardiac cycle and labelling a time interval of said distinctive feature as a cardiac cycle start time;
(c) labelling all subsequent time intervals in the current cardiac cycle by incrementing time intervals from said cardiac cycle start time until said distinctive feature is encountered in a next cardiac cycle;
(d) determining a peak in said digitized detection output for the current cardiac cycle and storing a time interval label identifying systole in the current cardiac cycle;
(e) determining a minimum in said digitized detection output for the current cardiac cycle and storing a time interval label identifying diastole in the current cardiac cycle;
(f) during the next cardiac cycle, counting a number of time intervals from a cardiac cycle start time of the next cardiac cycle in accordance with the time interval label identifying diastole for the current cardiac cycle and applying said pulses of infrared light to said arterial blood vessel of the patient for a duration of said diastolic time interval, and then counting a number of time intervals from said diastolic time interval in accordance with the time interval label identifying systole for the current cardiac cycle and applying said pulses of infrared light to said arterial blood vessel of the patient for a duration of said systolic time interval;
(g) when said infrared light is applied to said blood vessel of the patient, recording in a memory said at least one detection signal;
(h) repeating steps (a) through (e) for the next cardiac cycle;
(i) determining whether diastole and systole for the next cardiac cycle actually occurred within a predetermined number of time intervals from when said pulses of infrared light were applied to said blood vessel of the patient in step (f); and
(j) if it is determined in step (i) that diastole and systole for the next cardiac cycle actually occurred within said predetermined number of time intervals from when said pulses of infrared light were applied to said arterial blood vessel of the patient in step (f), calculating the concentration of said at least one predetermined constituent from said recorded at least one detection signal, but if it is determined in step (i) that diastole and systole for the next cardiac cycle did not actually occur within said predetermined number of time intervals from when said pulses of infrared light were applied to said arterial blood vessel of the patient in step (f), erasing said recorded at least one detection signal from said memory.

24. A method as in claim 23, including the further step of repeating steps (a) through (j) until the concentration of said at least one predetermined constituent is calculated from said recorded at least one detection signal a plurality of times, and then averaging the plurality of calculated concentrations to get an average concentration value for said at least one predetermined constituent of the patient's blood.

25. A method as in claim 20, wherein said concentration determining step includes the step of forming a ratio R=(Sys L1−Dias L1)/(Sys L2−Dias L2), where Sys L1 is a detected systolic phase signal at said one wavelength, Dias L1 is a detected diastolic phase signal at said one wavelength, Sys L2 is a detected systolic phase signal at said another wavelength, and Dias L2 is a detected diastolic phase signal at said another wavelength.

26. A method as in claim 25, wherein said concentration determining step includes the step of calculating the concentration of said at least one predetermined constituent (n) of the patient's blood in accordance with the following equation:

$$C.C._n = B + \sum_{x=1}^{x=(m-1)} \left[ \sum_{y=1}^{y=p} C_{x,y}*[Ln(R_x)]^y \right] + \sum_{z=1}^{z=p} D_z*[L_n(R_1)*Ln(R_2) \ldots *Ln(R_n)]^z \quad [\text{EQ. (3)}]$$

where:
$C.C._n$ is the concentration of said at least one predetermined constituent n;
B, $C_{x,y}$ and $D_z$ are empirically determined calibration coefficients; m is the number of detection and reference wavelengths used;
p is the highest order of polynomial used; and Ln is a natural log function.

* * * * *

UNITED STATES PATENT AND TRADEMARK OFFICE
CERTIFICATE OF CORRECTION

PATENT NO. : 5,313,941
DATED : May 24, 1994
INVENTOR(S) : Braig et al.

It is certified that error appears in the above-identified patent and that said Letters Patent is hereby corrected as shown below:

Column 2, line 40, change "were" to --where--.

Column 3, line 45, change "were" to --where--.

Column 5, line 1, change "maybe" to --may be--.

Column 5, line 31, change "were" to --where--.

Column 9, line 59, delete "changing".

Column 10, line 35, change "KANTHAL TM" to --KANTHAL™--.

Column 10, line 58, change "optical" to --Optical--.

Column 15, line 68, change "be-" to --be--.

Column 16, line 12, change "Caused" to --caused--.

Column 16, line 17, change "the" to --that--.

Column 18, line 2, change "said" to --so--.

Signed and Sealed this

Sixth Day of June, 1995

BRUCE LEHMAN

*Attest:*

*Attesting Officer*  *Commissioner of Patents and Trademarks*